US 6,606,817 B2
(12) United States Patent
Oi et al.

(10) Patent No.: US 6,606,817 B2
(45) Date of Patent: *Aug. 19, 2003

(54) ABOVE GROUND NON-EDIBLE FORAGING MATRIX CONFIGURATIONS FOR ARTHROPOD CONTROL

(75) Inventors: Faith M. Oi, Gainesville, FL (US); Philip G. Koehler, Gainesville, FL (US)

(73) Assignee: University of Florida, Gainesville, FL (US)

(*) Notice: Subject to any disclaimer, the term of this patent is extended or adjusted under 35 U.S.C. 154(b) by 0 days.

This patent is subject to a terminal disclaimer.

(21) Appl. No.: 10/098,017
(22) Filed: Mar. 13, 2002
(65) Prior Publication Data
US 2002/0134003 A1 Sep. 26, 2002

Related U.S. Application Data

(63) Continuation-in-part of application No. 09/942,341, filed on Aug. 29, 2001, which is a continuation-in-part of application No. 09/525,086, filed on Mar. 14, 2000, now Pat. No. 6,298,597.
(60) Provisional application No. 60/243,905, filed on Oct. 27, 2000, and provisional application No. 60/159,266, filed on Oct. 13, 1999.

(51) Int. Cl.$^7$ .............. A01M 1/20; A01M 25/00
(52) U.S. Cl. .............. 43/131; 43/132.1; 43/107; 43/124; 43/121; 106/15.05; 424/411; 424/84
(58) Field of Search .............. 43/131, 132.1, 43/107, 124, 121; 106/15.05; 424/411, 84

(56) References Cited

U.S. PATENT DOCUMENTS 16,949 A * 3/1857 Gaskins ............. 162/93

(List continued on next page.)

FOREIGN PATENT DOCUMENTS

GB 2306886 * 5/1997 .......... A01N/25/08

OTHER PUBLICATIONS

*Laboratory Evaluation I of Insecticides for Control of Tar-*

(List continued on next page.)

Primary Examiner—Peter M. Poon
Assistant Examiner—Andrea M. Valenti
(74) Attorney, Agent, or Firm—Brian S. Steinberger; Law Offices of Brian S. Steinberger, P.A.

(57) ABSTRACT

Above ground kits for controlling arthropods such as termites, carpenter ants, fire ants, roaches, combinations, and the like. Embodiments can include mounting a chamber on the inside and outside of a manmade structure such as a house, a building, and a shed. Additionally, the invention can be mounted on a foundation beneath the structure. Furthermore, the above ground invention can be mounted on a side of a fence. Still furthermore, the invention can be placed on the sides of natural items that need protection such as trees, and the like. And still furthermore, the invention can be attached to a planter. Methods for mounting can include adhesive layers such as peel and stick tape, as well as removable fasteners such as hook and loop fasteners. Other fasteners can include nails, screws and stake type members. The chambers can be wrapped in shrink wrap, and the like. The chamber can be cylindrical disc shape having one closed end and closed sides, such as plastic cup, Petri dish, and the like, and can be non-opaque so that interior contents can be viewed from outside. Additionally, the upper end of the chamber can be opened with a removable lid so that chambers can be reused over time. The lower end can include a layer of an edible non-toxic material such as a layer of foam, and the like. On top of the edible layer, can be a layer of a non-edible foraging matrix that contains the slow-acting non-repellent toxicant within the foraging matrix, and this layer can be visible through the top of the chamber. Arthropods climbing up the sides of manmade and natural structures can then pass through the edible foam type layer in the open end of the chamber and then forage into the layer containing the non-edible material which is mixed with the slow-acting non-repellent toxicants. Arthropods leave the above ground chamber in the same direction they came and take the toxicant back to their galleries and colonies where the arthropods will be killed over time.

34 Claims, 11 Drawing Sheets

U.S. PATENT DOCUMENTS

| | | | | |
|---|---|---|---|---|
| 1,634,648 A | * | 7/1927 | Cardinet | 43/107 |
| 1,759,359 A | * | 5/1930 | Lennox | 43/131 |
| 1,769,408 A | * | 7/1930 | Andrews | |
| 2,219,403 A | * | 10/1940 | Sennewald | 206/527 |
| 2,931,140 A | | 4/1960 | Laffler | 47/48.5 |
| 3,835,578 A | | 9/1974 | Basile | 43/132 |
| 3,940,875 A | | 3/1976 | Basile | 43/124 |
| 4,043,073 A | | 8/1977 | Basile | 43/124 |
| 4,625,474 A | * | 12/1986 | Peacock et al. | 137/357 |
| 4,709,503 A | * | 12/1987 | McQueen | 43/114 |
| 5,435,096 A | | 7/1995 | Nekomoto | 43/112 |
| 5,592,774 A | | 1/1997 | Galyon | 43/124 |
| 5,778,596 A | | 7/1998 | Henderson et al. | 43/132.1 |
| 5,815,090 A | | 9/1998 | Su | 340/870.16 |
| 5,918,410 A | * | 7/1999 | Knuppel | 43/131 |
| 5,935,943 A | | 8/1999 | Asai et al. | 514/63 |
| 5,950,356 A | | 9/1999 | Nimocks | 43/131 |
| 5,979,108 A | * | 11/1999 | Adams | 43/121 |
| 6,014,834 A | * | 1/2000 | Ferland | 43/121 |
| 6,052,066 A | | 4/2000 | Su | 340/870.16 |
| 6,079,150 A | | 6/2000 | Setikas | 43/132.1 |
| 6,195,934 B1 | * | 3/2001 | Megargle et al. | 43/131 |
| 6,370,812 B1 | | 4/2002 | Burns et al. | 43/124 |
| 6,397,516 B1 | | 6/2002 | Su | 43/124 |

OTHER PUBLICATIONS nished Plant Bug in Mississippi, research report from University of Mississippi website, 1995. (pp. 1 and 2 of 3).

*Letter to Kandy Walker Duke at Rhone Merieux from New York State Department of Environmental Conservation*, letter dated Feb. 7, 1997, obtained from website address: pmep.cce.cornell.edu, updated Dec. 16, 1997. (pp. 1&2 of 3).

*Rhône–Poulenc's Fipronil give approval for Clorox Products*, press release from library section of website www.rhone–poulenc.com, Aug. 5, 1997, last updated Feb. 11, 1998. 1 page.

*Toxicity and Degradation of Fipronil Applied to Cotton for Control of Boll Weevils*, Joseph E. Mulrooney and Deepa Goli, interpretive summary for TEKTRAN website address www.nal.usda.gov, Dec. 3, 1997. p. 1 of 2.

*Fipronil*, NPTN fact sheet on Fipronil from National Pesticide Telecommunications Network website, 5 pages, 12/97.

*Prospective Study Comparing Fipronil with dichlorvos/fenitrothion and methoprene/pyrethrins in control of Flea Bite Hypersensitivity in Cats*, R.G. Harvey, E.J. Penaliggon, and P. Gautier, Veterinary Record (1997), www.inno–vet.com. p. 1.

Website www.peteducation.com, general information on Fipronil as used in flea prevention and treatmenet 1997, 3 pages.

*Control of Corn Root Worm in Green Peas*, WSU cooperative extension reserach report, Washington State University, www.agsyst.wsu.edu, last updated Jul. 24, 2000. pp. 1 to 5.

*Residue Analysis of Fipronil and its Metabolites Observec in Leek Samples*, Guido Goller, Patrick Duchene and Marc Maestracci, report available on website www.chemsoc.org, no date listed, one page.

*Evaluation of Fipronil for residual control of mole crickets on turfgrass*, Table of results using Fipronil to treat mole crickets on turfgrass, no date listed, one page.

*Field Trials to Evaluate the Efficacy of Fipronil (regent R) for Controlling Rice Insects Under Different Formulations*, Luuong Minh Chau, report posted on website www.chemsoc.org, no date listed, two pages.

*Maxforce Bait Gel–FC–German Roaches*,www.roachcontrol.com, website advertisement for Maxforce Gel FC, no date listed, three pages.

* cited by examiner

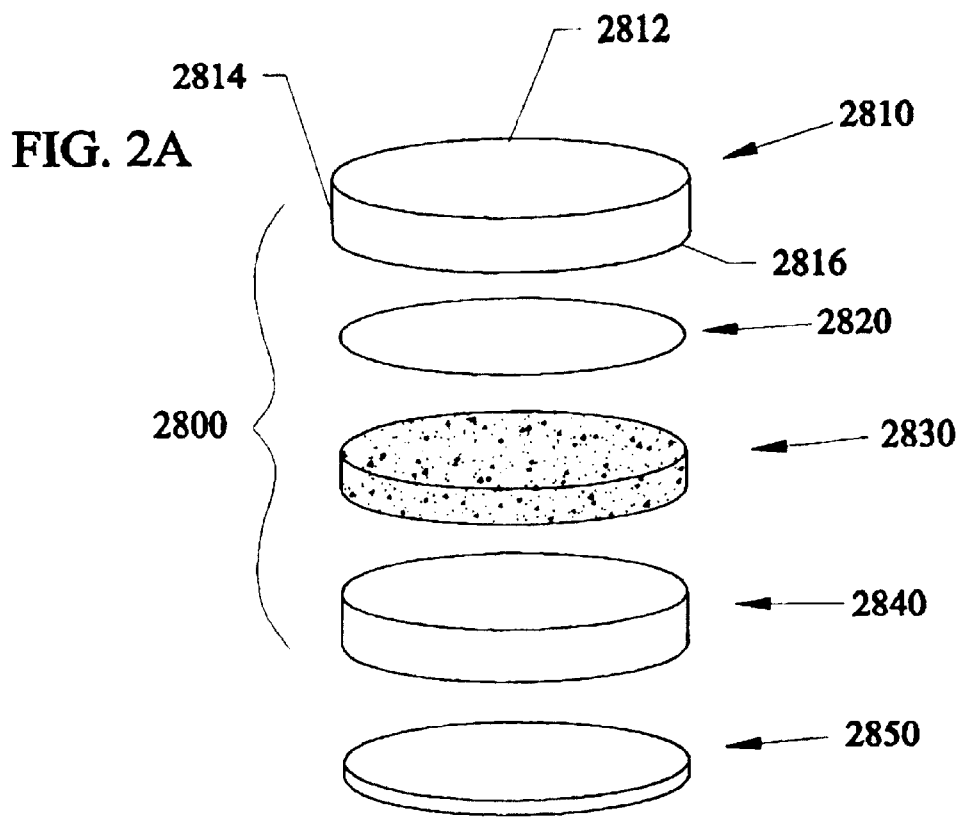
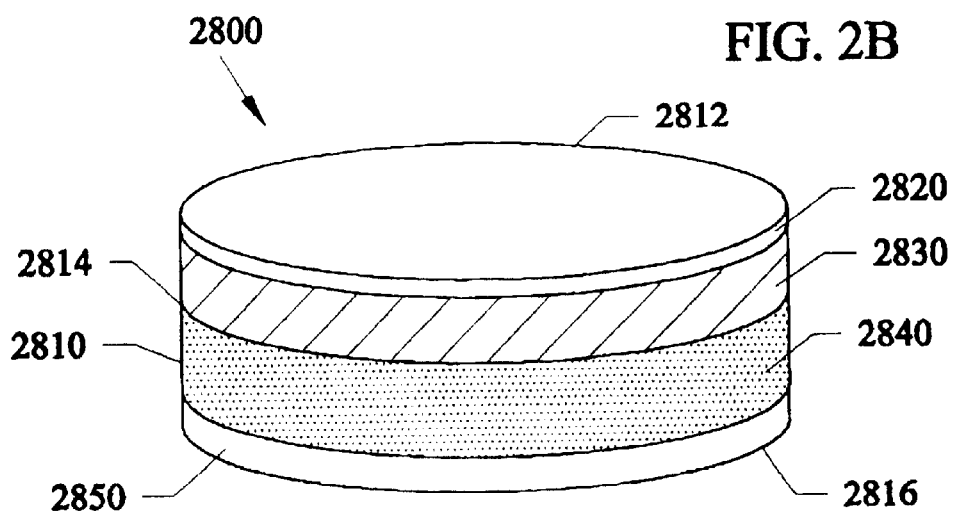

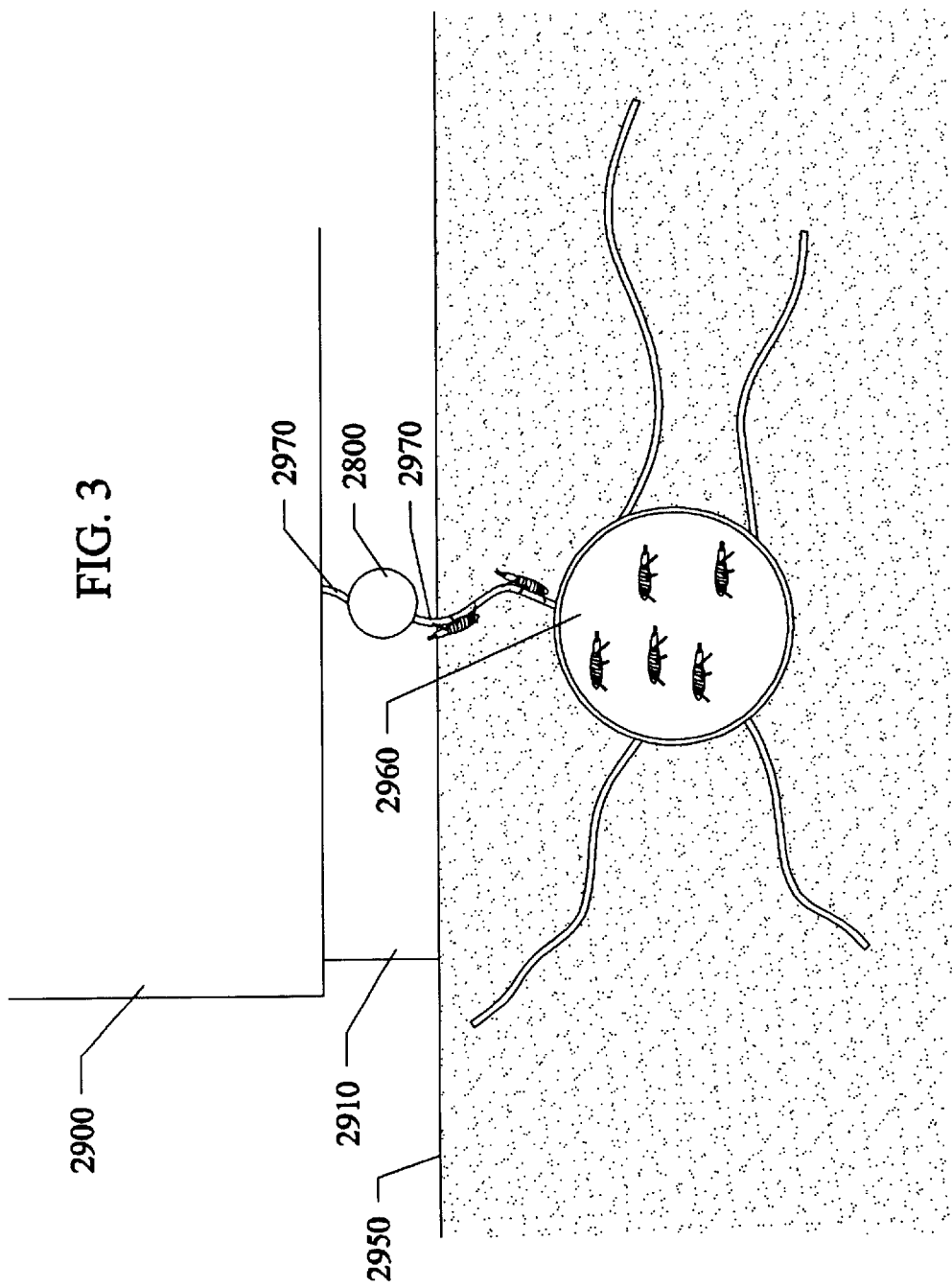

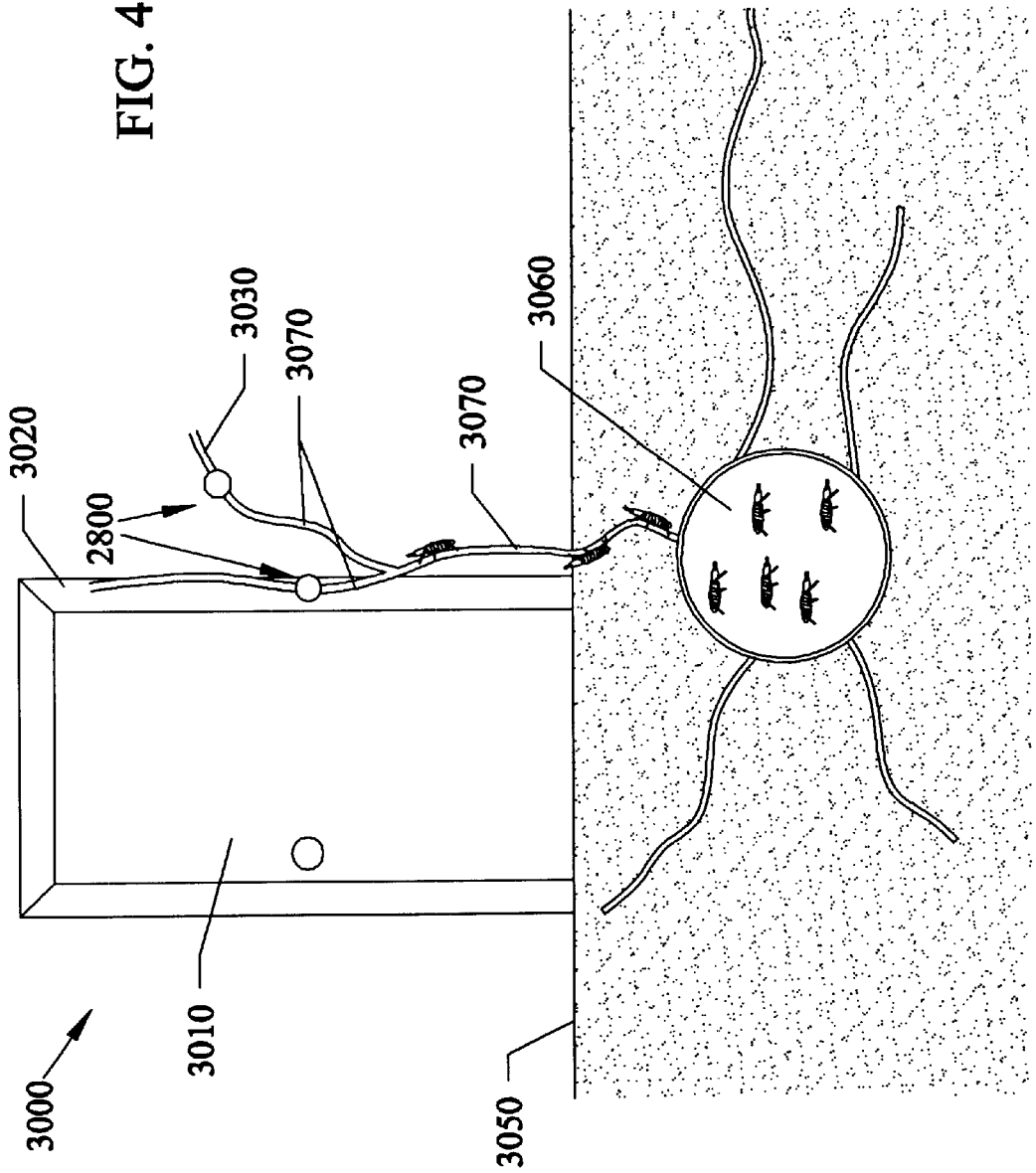

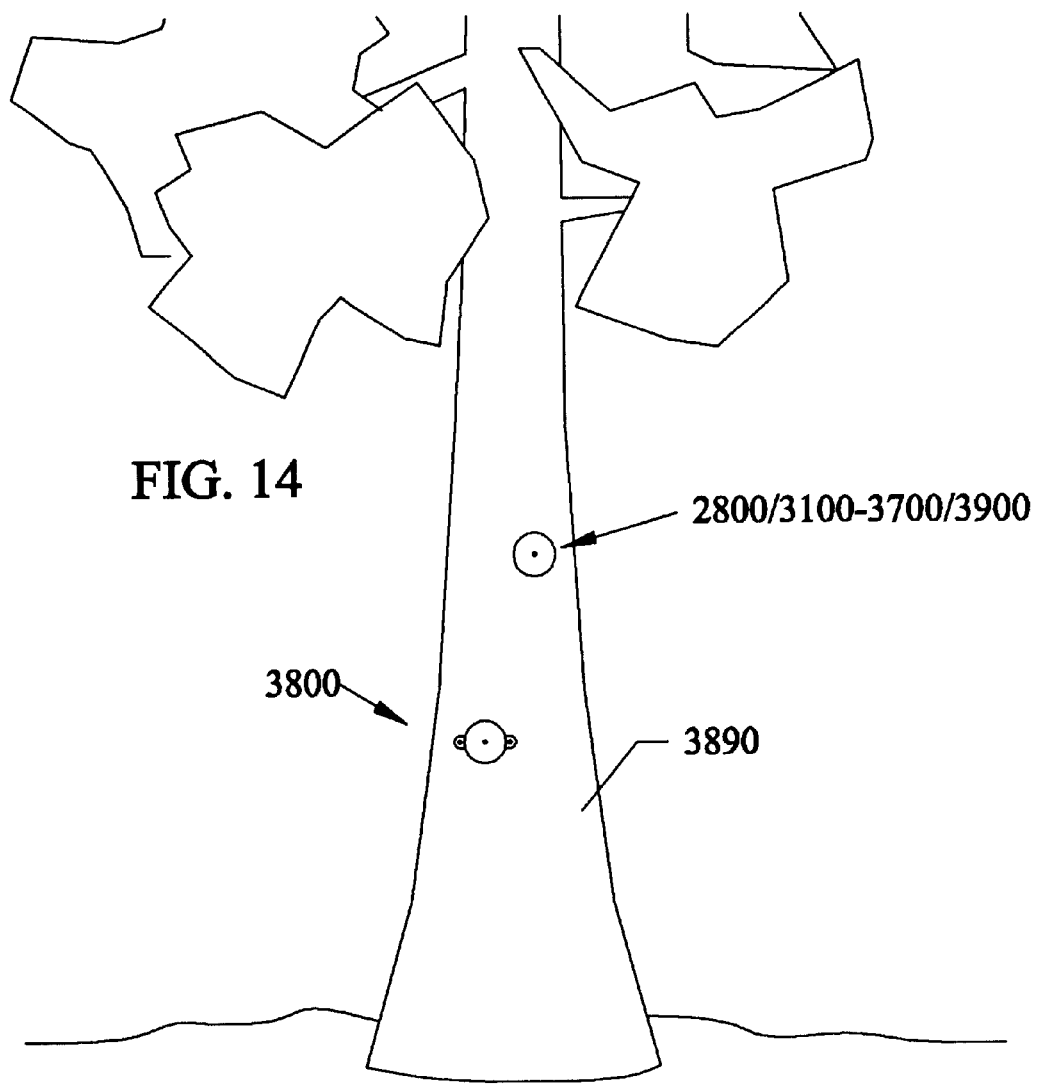

ABOVE GROUND NON-EDIBLE FORAGING MATRIX CONFIGURATIONS FOR ARTHROPOD CONTROL

This invention relates to above ground controls for arthropods such as termites, carpenter ants, fire ants and roaches, and in particular to apparatus and methods for using a non-toxic food source to attract the arthropods into housings having a non-edible foraging matrix treated with slow acting and non-repellant toxicants, that causes the arthropods to take the toxicants back to galleries and living areas in their colonies, and this invention is a Continuation-In-Part of U.S. application Ser. No. 09/942,341 filed Aug. 29, 2001, which claims the benefit of priority to U.S. Provisional Application No. 60/243,905 filed Oct. 27, 2000, by the same inventors and assignee as the subject invention, and which also is a Continuation-In-Part of U.S. application Ser. No. 09/525,086 filed Mar. 14, 2000 by the same inventors and a co-assignee of the subject invention which is now U.S. Pat. No. 6,298,597, and which claims the benefit of priority to U.S. Provisional Application No. 60/159,266 filed Oct. 13, 1999.

BACKGROUND AND PRIOR ART

Common nuisance pests that are of a primary concern for causing damage generally include arthropods such as termites, carpenter ants, fire ants and roaches. In southern areas especially Florida, termites are considered to be one of the most destructive arthropod pests for any manmade structures containing wood such as the framing in homes, as well as for causing destruction to natural wood containing items such as trees, and the like. termites and dry wood termites. Subterranean termites typically nest in the ground and usually maintain some sort of ground connection at all times. Dry wood termites usually start off in damaging pieces of wood materials, and do not require a ground connection. Between the two forms, the subterranean termites are the most damaging type of termites and usually enter structures such as buildings from surround soil adjacent to the structures.

Over the years there have been at least several methods of subterranean termite control. For example, the most common method of subterranean termite control requires soil underlying a structure to be treated with a termiticide barrier to prevent the termites from entering the structure from the ground. For example, a typical structure such as a house would have used hundreds of gallons of termiticide that would have been used to treat the soil underneath the house foundation.

From approximately 1950 to approximately 1988, a popular method for barrier treatment control for subterranean termites was chlorinated hydrocarbons. However, environmental concerns with those chemical treatments resulted in problems with the soil that could last up to approximately 35 years. Replacement chemicals for the chlorinated hydrocarbons were not popular since the replacement chemicals had a high rate of failure which resulted in extensive termite damage to the structures.

Problems with the barrier treatments became further compounded since builders have often been known to dump substantial amounts of termite edible building materials, such as wood and cardboard scraps, into the underlying soil that have served as guide lines for allowing the termites to then enter from the soil up and into the structures. These edible debris are a substantial food source, that increases the likelihood of termite infestation into the structure.

Over the years, different techniques have been developed and proposed to enhance the underground delivery of toxic insecticides beneath structures. See for example, U.S. Pat. Nos. 3,940,875 and 4,043,073 to Basile; and U.S. Pat. No. 4,625,474 to Peacock. However, many of these techniques and systems such as Basile '073 are concerned with trying to refresh the initial termiticide barrier by having the termites chew through a container with the toxicant (for example). Other examples of these techniques and systems allow for installing a piping system during the building construction process so that additional termiticide can be pumped under a slab of the building at intervals during construction. Furthermore, some of these techniques and systems such as the Basile '073 patent utilized a toxicant (for example, dieldrin) which has been banned by the EPA (Environmental Protection Agency) for termite treatment. Additionally, the pipes used in the pumping delivery systems have been known to often get clogged after installation making the pipe delivery systems not reliable nor usable overtime.

Other well-known subterranean termite treatment techniques and systems include bait techniques, which require termites to forage into a monitor that contains a non-toxic food source. Once termites infest the non-toxic food source, a food source laced with a toxicant (toxic bait) is replaced into the monitor. Termites continue to be recruited into the monitor and feed on the toxic bait. Consumption and trophallaxis (feeding other termites) of the toxic bait later causes many termites to die. See for example, U.S. Pat. No. 5,329,726 to Thome et al.; U.S. Pat. No. 5,899,018 to Gordon et al.; and U.S. Pat. No. 5,950,356 to Nimocks. However, these techniques generally require that the termites consume the toxic bait. Termites refuse to consume most toxicants. Therefore this technique is generally useful for only some 2 to 3 toxicants currently known in the world. Termites also refuse to consume bait food sources that are contaminated with molds or food sources that are too wet. These bait techniques do not use a non-edible foraging matrix (as described in the subject invention), such as but not limited to soil and sand, to cause the termites to tunnel therethrough and carry the non-edible particles treated with the toxicants to the galleries and living spaces of the colony, and thus contaminating the colonies. Most toxicants applied to non-edible foraging matrixes, except repellant pyrethroids, will be picked up and carried by the termites to other areas of their tunnel systems.

Other systems have been proposed but still fail to overcome the problems with the methods and applications described above. U.S. Pat. No. 3,972,993 to Kobayashi et al. requires a membrane be treated with a substance attractive to termites (due to the termite's innate searching and feeding behavior, termites are not attracted to food from a distance when allowed to forage without interference) so that when the termites chew through the membrane a toxic surface is contacted. U.S. Pat. No. 5,501,033 to Wefler delivers a liquid toxic food source for social insects such as yellowjackets and has very little use for termites. U.S. Pat. No. 5,609,879 to Myles requires the laborious harvesting of termites from the ground, sponging on an insecticidal epoxy, and returning it to the soil. U.S. Pat. No. 5,778,596 to Henderson et al. is a device for delivering toxic food for termites to consume. And U.S. Pat. No. 5,921,018 to Hirose provides foraging guidelines for termites to follow so the termites enter a device that captures and kills them.

There are additional problems with prior art treatments that use repellent liquids, non-repellent liquids, and baits. When using repellent liquids, the liquid barriers need to be applied in a perfectly continuous fashion. If gaps in the treatment exist, especially with repellent termiticides, such as those belonging to the pyrethroid class, the termites will forage and find the gaps in the treatment, increasing the probability of infesting the structure.

In non-repellent liquid treatments, the termites are not able to detect that they are in a treated area; hence the classification "non-repellent", and the termites die. A major drawback for non-repellent liquid treatments is that liquid termiticides in this class are still so new that there are questions about how long they will last in the soil, especially when exposed to sun and weather. The subject invention protects the foraging matrix from the sun and weather conditions in order to prolong its' usability, and the foraging matrix can be continuously replaced as necessary to recharge the system. The application of liquid termiticide barriers requires several hundred gallons of insecticide that is pumped under structures, such as houses, and can sometimes result in the contamination of the house interior, as well as water supply wells. Most homeowners have been known to want termicide applications that are less intrusive and disruptive.

Bait type station techniques and systems are again not practical since the bait stations require a food source that is palatable to termites. Selecting the appropriate food source can be difficult. While wood is a known food source, wood is very inconsistent in composition, so manufacturers don't like to use it with toxicants.

Other known food sources such as paper food sources have other problems. For example, if paper is not packed tightly enough, it will be emptied by termites and not be able to deliver enough toxicants to kill large numbers of termites. Most cellulose material will rot when placed in the soil. Once the cellulose material food source goes bad, termites will not feed, rendering the bait ineffective.

The subject invention uses a non-edible foraging matrix treated with a slow-acting non-repellent toxicant for above ground arthropod control methods and systems. Termites can put the particles of the treated matrix into their mouths when they tunnel through it, and many toxicants will work because they do not need to consume it and feed it to others. The particles are returned to the colony and incorporated into their tunnels. Termites that contact the particles die several days after the toxicant on the matrix particles are contacted. The behavior of the termites moves the treated foraging matrix from the exit and entrance opening of the device's chamber to contaminate their colony and tunnels.

SUMMARY OF THE INVENTION

A primary objective of the invention is to provide an above ground method and system for killing arthropods such as termites, carpenter ants, fire ants and roaches over time that safely disperses toxicants without allowing humans and pets to come into contact with the toxicants.

A secondary objective of the invention is to provide an above ground method and system for protecting manmade structures such as homes, buildings, fences and sheds from destructive arthropods such as termites, carpenter ants, fire ants and roaches.

A third objective of the invention is to provide an above ground method and system for protecting natural items such as trees, shrubbery, plants and gardens from destructive arthropods such as termites, carpenter ants, fire ants, and roaches.

The fourth objective of the invention is to provide an above ground method and system for using a non-toxic and edible food source to attract arthropods such as termites, carpenter ants, fire ants, and roaches, and causing the arthropods to then tunnel through non-edible particles that are treated with a slow-acting and non-repellent toxicant so that arthropods returning to their colonies will contaminate their galleries and living spaces with the toxicant.

A fifth objective of the invention is to provide an above ground method and system for using non-edible particles such as soil particles, sand particles, sand particles, and the like, and mixtures thereof for dispersing toxicants to arthropods such as termites, carpenter ants, fire ants and roaches that pass through tunnels, galleries and living spaces.

A sixth objective of the invention is to provide above ground systems and methods for treating arthropods such as termites, carpenter ants, fire ants, and roaches, that is easy and quick to apply to above ground structures and items.

A seventh objective of the invention is to provide above ground methods and systems for easily accessing arthropod controls without having to remove the controls from a premounted location.

Above ground surface methods and systems are included for killing arthropods such as termites, carpenter ants, fire ants, and roaches, to protect manmade structures such as homes, buildings, sheds and natural items such as but not limited to trees, shrubbery, plants and gardens.

The above ground methods and systems can include positioning the embodiment against a structure or item that is to be protected. Inside the chamber is an open bottom end with an edible non-toxic food source such as foam which can be jammed into the open bottom end of the chamber. Above the food source can be a foraging matrix having a non-edible foraging material mixed with a slow-acting non-repellent toxicant. The side of the non-toxic food source that is positioned against the structure or item can include a fastener surface such as but not limited to peel and stick tape, hook and loop fasteners, and the like, which allows the embodiments to be attached to various manmade and natural structures and items. Additionally, the embodiments can be attached by novel fastening arrangements using fasteners such as screws, nails, and stakes, and the like.

Additional embodiments can include removable caps that can be either screwed on, snapped, on, or hingedly attached to the top of the chamber to allow the contents of the chamber to be replenished without having to remove the entire embodiment from a preattached location.

Further objects and advantages of this invention will be apparent from the following detailed description of a presently preferred embodiment which is illustrated schematically in the accompanying drawings.

BRIEF DESCRIPTION OF THE FIGURES

FIG. 2A is an exploded view of a first preferred embodiment with fastener backing.

FIG. 2B is an assembled view of the preferred embodiment of FIG. 2A.

FIG. 3 shows the preferred embodiment of the preceding figures being applied to a foundation/slab of a building structure FIG. 4 shows the preferred embodiment of the preceding figures being applied to interior/exterior walls of a building/housing/shed structure.

FIG. 12 shows a sixth embodiment of a top view of the above ground invention for allowing the invention to be physically attached to natural structures such as trees, and the like.

FIG. 14 shows the embodiments of FIGS. 12–13 and the preceding embodiments being attached to various locations on a tree.

DESCRIPTION OF THE PREFERRED EMBODIMENTS

Before explaining the disclosed embodiments of the present invention in detail it is to be understood that the invention is not limited in its application to the details of the particular arrangements shown since the invention is capable of other embodiments. Also, the terminology used herein is for the purpose of description and not of limitation.

Below ground embodiments for arthropod control are described in detail in the parent application Ser. No. 09/525,086 filed Mar. 14, 2000 by the same inventors and a co-assignee as that of the subject invention, issued as U.S. Pat. No. 6,298,597, which subject matter is incorporated by reference.

Further below ground embodiments for arthropod control are also described in detail in parent application Ser. No. 09/942,341 filed Aug. 29, 2001 to the same inventors and assignee as that of the subject invention, the subject matter of which is also incorporated by reference.

First Embodiment

Figure 1A:
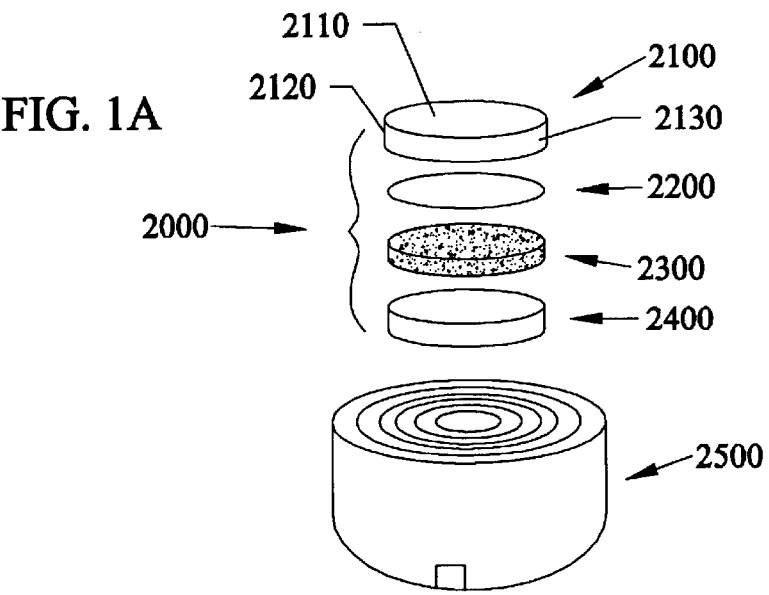
FIG. 1A is an exploded view of an experimental layout for an above ground application of the invention.
Figure 1B:
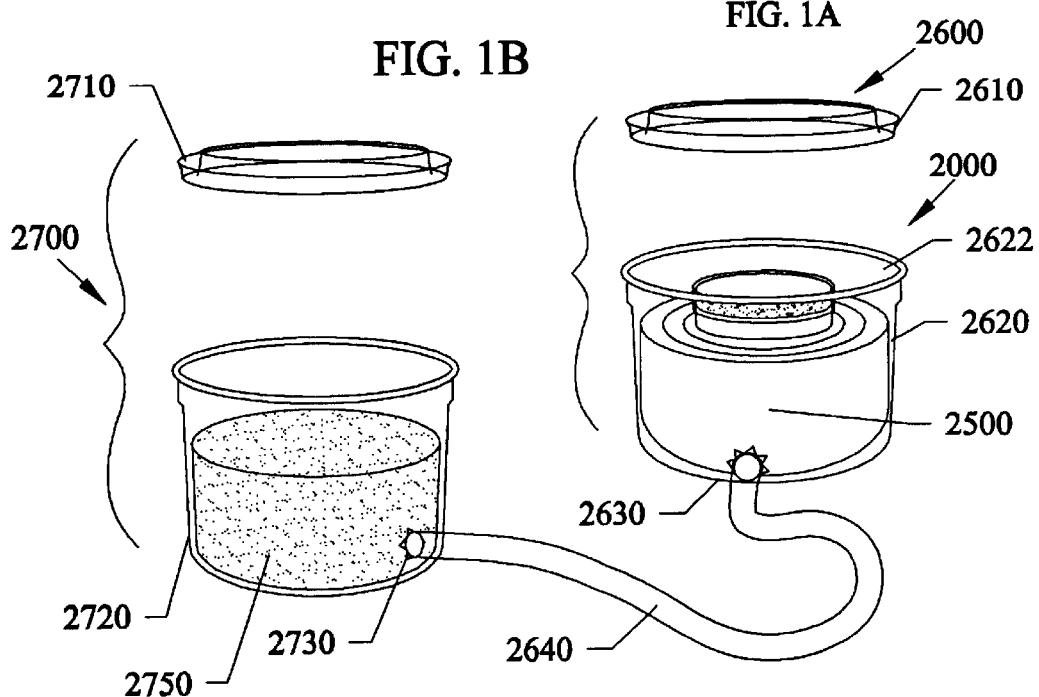
FIG. 1B is an assembled view of the layout of FIG. 1A with a soil source having arthropods.

FIG. 1A is an exploded view of an experimental layout 200 for an above ground application of the invention. FIG. 1B is an assembled view of the layout 2000 of FIG. 1A with a soil source 2750 having arthropods. Referring to FIGS. 1A–1B, the experimental layout included a rolled cardboard base 2500, which serves as an attractive food source for arthropods such as termites. A chamber 2100 having a closed top 2110, closed sides 2120 and open bottom 2130 can have a diameter of approximately 5 cm, and a depth of approximately 1.3 cm. Inside the chamber 2100 can be a thin layer 2200 such as an edible non-toxic food source such as a cellulose material such as but not limited to rolled up paper towels, cardboard, and the like.

A disc shape of a foraging matrix 2300 containing non-edible particles can be mixed with a slow-acting non-repellent toxicant having a thickness of approximately. 7 cm and a diameter slightly less than the diameter of the chamber 2100 can be positioned inside of the chamber 2100. Next a disc of an edible non-toxic food source 2400, such as but not limited to foam, having a thickness of approximately 1.2 cm and a diameter barely smaller than that of the chamber 2100 can be placed into the chamber open end 2130 where it is tightly held in place.

The chamber 2100 with stacked contents can have its' open bottom end placed inside of a plastic see-through container 2600 where it is positioned on top of rolled up food source 2500. The cover can be snapped onto the top of the container 2600. Along a lower edge of side 2620 of container 2600 is a small opening 2630 which allows for one end of a flexible hollow tube 2640 to be placed therein. The opposite end of tube 2640 can be connected to an opening 2730 in a lower edge of side 2720 of container 2700. Within container 2700 can be a soil 2750 that contains known colonies of active termites. A removable lid 2710 closes the upper opening of the container 2700.

Referring to FIGS. 1A–1B, active termites can crawl from container 2700 through tubing 2640 to enter the lower part of container 2600, where the termites start eating through the edible food source 2500, and then reach the edible non-toxic food source disc 2400 within the opening end 2130 of the chamber 2100. Next the termites can forage through the non-edible foraging matrix that is mixed with the slow-acting non-repellent toxicant layer 2300.

The experimental conditions for the layout of FIGS. 1A–1B will now be described. Two plastic containers (Solo deli cups, 16 oz.) were connected at the base by about 58 cm of Tygon tubing (¼"I.D.). Tubing was filled with builder's sand. One of the deli cups was filled with approximately 150 g of builder's sand. The other deli cup contained a roll of cardboard (5.8×210.0 cm). A Petri dish (Falcon 1007, approximately 60 mm diameter by approximately 15 mm high) was designated as the above ground application device. The Petri dish contained 3 layers of paper towel (Premiere Roll Towels, Kimberly-Clark, Roswell, Ga.), a layer of treated soil (approximately 16 g, non-edible foraging matrix), and a piece of foam, which held the soil in place and allowed the termite's additional tunneling material. The non-edible foraging matrix was treated with approximately 12.5 ppm chlorphenapyr. The above ground device was placed in the center of the cardboard roll. One thousand worker termites were introduced into the deli cup that contained the builder's sand. Termites were allowed to forage and feed for approximately one month. After one month, the testing apparatus was dismantled. Surviving termites were counted and soil removed from the above ground application device weighed.

Table 1 shows different dated trials having five test samples each using Chlorfenapyr as the slow-acting non-repellant toxicant interspersed with the non-edible foraging matrix, compared to a untreated control samples that do not have any slow-acting non-repellant toxicants.

TABLE 1

Above Ground With Paper

Chlorfenapyr 12.5 ppm  1
Start: 8/3/2002
End: 9/6/2002
1000 worker termites

| Treatment | Rep | Soil and Paper Removed | Ave. | Live Termites | Ave. | Mortality (%) | Ave. |
|---|---|---|---|---|---|---|---|
| Chlorfenapyr 12.5 ppm | 1 | 5.009 | 5.078 | 128 | 26.8 | 87.2 | 97.32 |
| Chlorfenapyr 12.5 ppm | 2 | 3.9209 | | 6 | | 99.4 | |
| Chlorfenapyr 12.5 ppm | 3 | 4.6704 | | 0 | | 100 | |
| Chlorfenapyr 12.5 ppm | 4 | 5.4268 | | 0 | | 100 | |
| Chlorfenapyr 12.5 ppm | 5 | 6.3641 | | 0 | | 100 | |
| Control | 1 | 7.3613 | 7.81 | 719 | 727 | 28.1 | 27.3 |
| Control | 2 | 0 | | 705 | | 29.5 | |
| Control | 3 | 9.2634 | | 737 | | 26.3 | |
| Control | 4 | 12.0027 | | 749 | | 25.1 | |
| Control | 5 | 10.425 | | 725 | | 27.5 | |

Chlorfenapyr 12.5 ppm  2
Start: 9/13/2002
End: 10/17/2002
1000 worker termites

| Treatment | Rep | Soil and Paper Removed | Ave. | Live Termites | Ave. | Mortality (%) | Ave. |
|---|---|---|---|---|---|---|---|
| Chlorfenapyr 12.5 ppm | 1 | 1.8367 | 1.425 | 170 | 270.8 | 83.17 | 73.19 |
| Chlorfenapyr 12.5 ppm | 2 | 0 | | 581 | | 42.48 | |
| Chlorfenapyr 12.5 ppm | 3 | 0 | | 603 | | 40.3 | |
| Chlorfenapyr 12.5 ppm | 4 | 2.9156 | | 0 | | 100 | |
| Chlorfenapyr 12.5 ppm | 5 | 2.3727 | | 0 | | 100 | |
| Control | 1 | 7.8217 | 8.342 | 605 | 543.6 | 40.1 | 46.18 |
| Control | 2 | 8.0771 | | 315 | | 68.81 | |
| Control | 3 | 11.0171 | | 544 | | 46.14 | |
| Control | 4 | 5.5126 | | 633 | | 37.33 | |
| Control | 5 | 9.2819 | | 621 | | 38.51 | |

In the first trial, there was an average of approximately 97.3% mortality in termites that were exposed to approximately 12.5 ppm chlorfenapyr with the above ground application device. Mortality in the controls was significantly less at approximately 27%. In the second trial, there was an average mortality of 73.2%. However, termites did not enter two of the above ground applications and were therefore not exposed to chlorfenapyr. If the data from the uninvaded above ground application devices are eliminated, and average mortality is taken on only those replications where termites invaded the application device, then mortality is 94.4%. Control mortality for all units was approximately 46.2%, which is high, but still less than mortality in treatment units. The average mortality for both trials where treatment units have been invaded is approximately 96.2%. The average control is approximately 37.5%. The test data demonstrates that the above ground application device can kill termites under the described conditions.

Additionally, for those units where termites invaded it, the average amount of soil moved in application devices that were treated was approximately 4.06 g, while the average amount moved in control units was approximately 8.97 g.

For the above ground arthropod control invention embodiments, the slow-acting non-repellant toxicant can include but not be limited to chlorfenapyr, Fipronil, thiomethoxam, imidacloprid, hydramethylnon, sulfuramid, IGRs such as but limited to Hexaflumuron, lurfenuron, diflubenuron, and the like. The slow-acting non-repellant toxicants can be intermixed with any non-edible foraging matrix such as but not limited to builder's sand, Alachua Fine Soil, and the like, as described in the parent applications to the subject inventions which are incorporated by reference.

FIG. 2A is an exploded view of a first preferred embodiment 2800 with fastener backing 2850. FIG. 2B is an assembled view of the preferred embodiment 2800 of FIG. 2A. Referring to FIGS. 2A–2B, a chamber 2810 such as a cylindrical disc, plastic petri dish, and the like, can have a closed top 2812, closed sides 2814, open bottom 2816, having dimensions of approximately 5 cm in diameter and approximately 1.3 cm in height. The closed top 2812, and/or the entire chamber 2810 can be made of a non-opaque material to allow users to see the contents inside the chamber 2810. Inside the chamber 2800 against the top 2812, can be a thin layer 2820 of an edible food source such as but not limited to cellulose, and the like. Underneath the layer 2820 can be a foraging matrix 2820 having a thickness of approximately. 7 cm and a diameter slightly less than that of the chamber 2810. The foraging matrix consists of non-edible particles mixed with a slow-acting non-repellent toxicant 2830. Underneath the foraging matrix 2830 can be a disc layer 2840 of an edible non-toxic food source such as foam, and the like. The disc layer 2840 can have a thickness of approximately 1.2 cm and a diameter barely slightly smaller than the diameter of the chamber 2810 so that the disc layer tightly fits within the open end 2816 of the chamber 2810.

Covering the outer exposed side of the disc 2840 can be a fastening member 2850 which allows the chamber to be fastened to various support surfaces. The fastening member can be an adhesive layer. The fastening member can be peel and stick tape, which allows the chamber to easily be applied to any surface when needed. Additionally, the fastening member can be a removable fastener such as but not limited to hook and loop fasteners, and the like.

FIG. 3 shows the preferred embodiment of the preceding figures being applied to a foundation/slab 2910 of a building structure 2900 such as a house, a building, a shed, and the like. Colonies of arthropods 2960 such as termites, below ground surface 2950 are known to build above ground tunnels 2970 on sides of foundations/slabs 2910 in order to travel to edible food sources in the structure 2900. Such edible food sources in a structure 2900 can include but not be limited to wood framing, wood siding, wood flooring, interior wood products, and the like, and combinations thereof.

Referring to FIG. 3, placing the above ground chamber 2800 with its' open end and fastening member surface onto the side of a foundation/slab 2910 can be an attractant food source for the termites. Furthermore, placing the novel above ground chamber directly in the path of a known above ground tunnel 2970 can have the effect of interrupting the travel route of the crawling arthropods from damaging the structure 2900. As previously described, arthropods, such as subterranean termites will bring the slow-acting non-repellent toxicants back to their spaces 2960 such as their galleries and colonies which will kill the arthropods over time.

FIG. 4 shows the preferred embodiment of the preceding figures being applied to interior/exterior walls of a building/housing/shed structure 3000. Colonies of arthropods 3060 such as termites, below ground surface 3050 are known to build above ground tunnels 3070 on sides of walls 3030, and other wall surface components such as door molding 3020 while traveling to edible food sources in the structure 3000. Such edible food sources in a structure 3000 can include but not be limited to wood doors, wood molding, wood framing, wood siding, wood flooring, interior wood products, and the like, and combinations thereof.

Referring to FIG. 4, placing the above ground chamber 2800 with its' open end and fastening member surface onto the side walls 3030 and door molding 3020 can be an attractant food source for the termites. Furthermore, placing the novel above ground chambers 2800 directly in the path of a known above ground tunnel 3070 can have the effect of interrupting the travel route of the crawling arthropods from damaging the structure described, arthropods, such as subterranean termites will bring the slow-acting non-repellent toxicants back to their spaces 3060 such as their galleries and colonies which will kill the arthropods over time.

Figure 5:
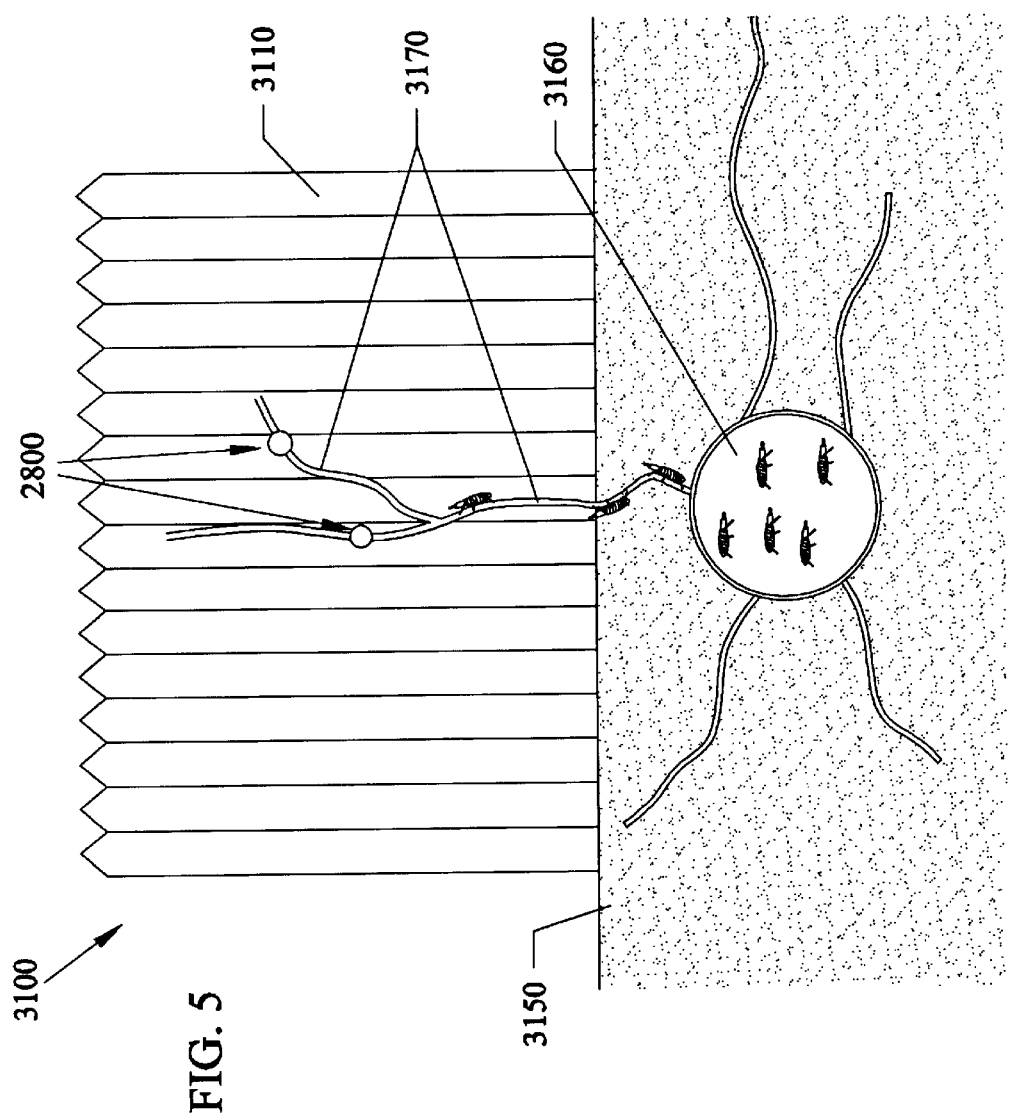
FIG. 5 shows the preferred embodiment of the preceding figures being applied to the exterior surface of a fence.

FIG. 5 shows the preferred embodiment of the preceding figures being applied to the exterior surface 3110 of a fence 3100, such as a wooden fence and the like. Colonies of arthropods 3160 such as termites, below ground surface 3150 are known to build above ground tunnels 3170 on sides of outdoor manmade type structures 3110 such as wood fences in order to travel to edible food sources in the structure 3110.

Referring to FIG. 5, placing the above ground chamber 2800 with its' open end and fastening member surface onto the sides 3110 of a fence structure 3100 can be an attractant food source for the termites. Furthermore, placing the novel above ground chamber directly in the path of a known above ground tunnel 3170 can have the effect of interrupting the travel route of the crawling arthropods from damaging the structure 3100. As previously described, arthropods, such as subterranean termites will bring the slow-acting non-repellent toxicants back to their spaces 3160 such as their galleries and colonies which will kill the arthropods over time.

Figure 6:
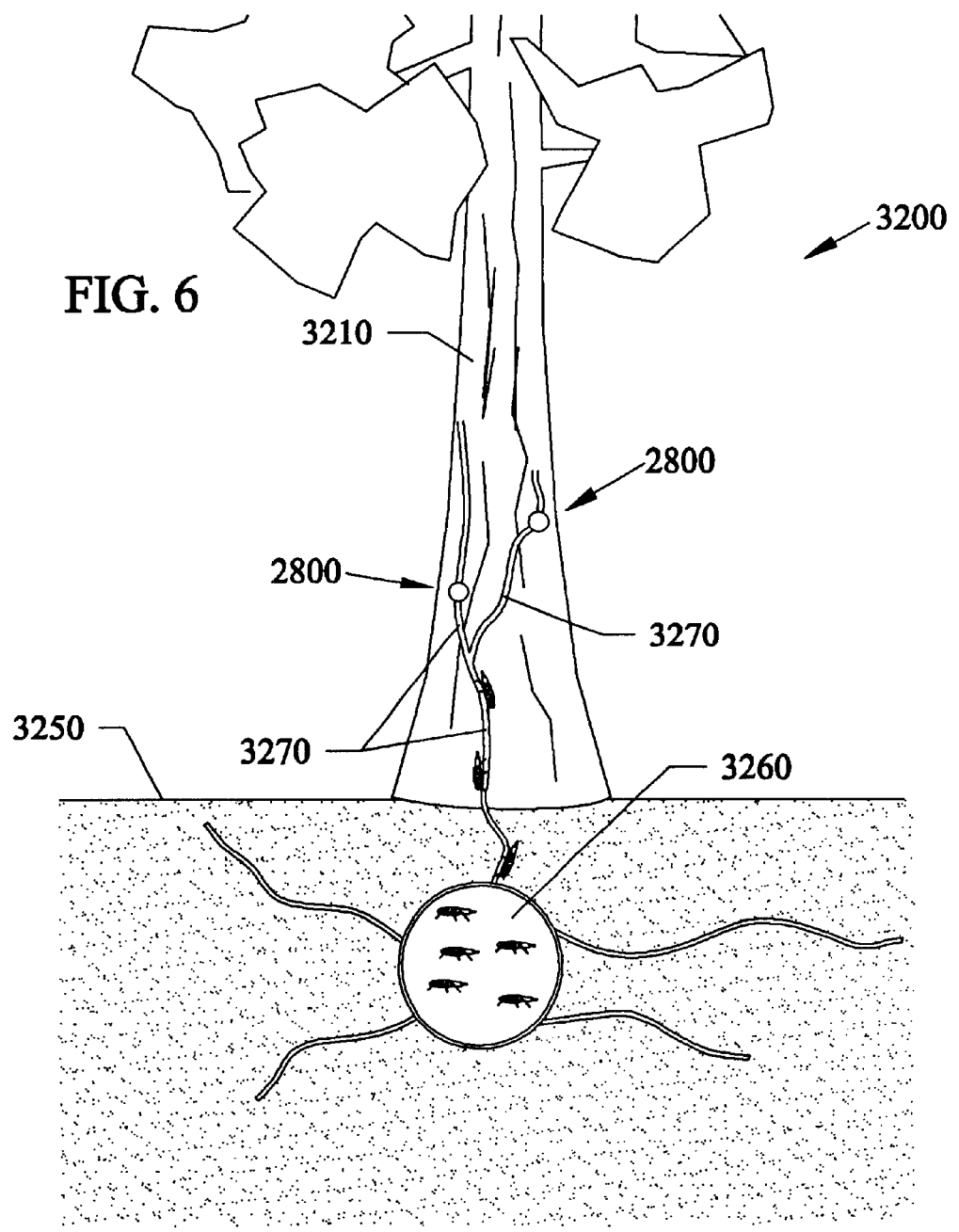
FIG. 6 shows the preferred embodiment of the preceding figures being applied to a tree.

FIG. 6 shows the preferred embodiment of the preceding figures being applied to a tree 3200. Colonies of arthropods 3260 such as termites, below ground surface 2950 are known to build above ground tunnels 3270 inside and on the sides 3210 of trees 3200 in order to travel to edible food sources such as the tree 3200.

Referring to FIG. 6, placing the above ground chamber 2800 with its' open end and fastening member surface on the tree 3200 can be an attractant food source for the termites. Furthermore, placing the novel above ground chamber directly in the path of a known above ground tunnel 3270 can have the effect of interrupting the travel route of the crawling arthropods from further damaging the tree 3200. As previously described, arthropods, such as subterranean termites will bring the slow-acting non-repellent toxicants back to their spaces 3260 such as their galleries and colonies which will kill the arthropods over time.

Figure 7:
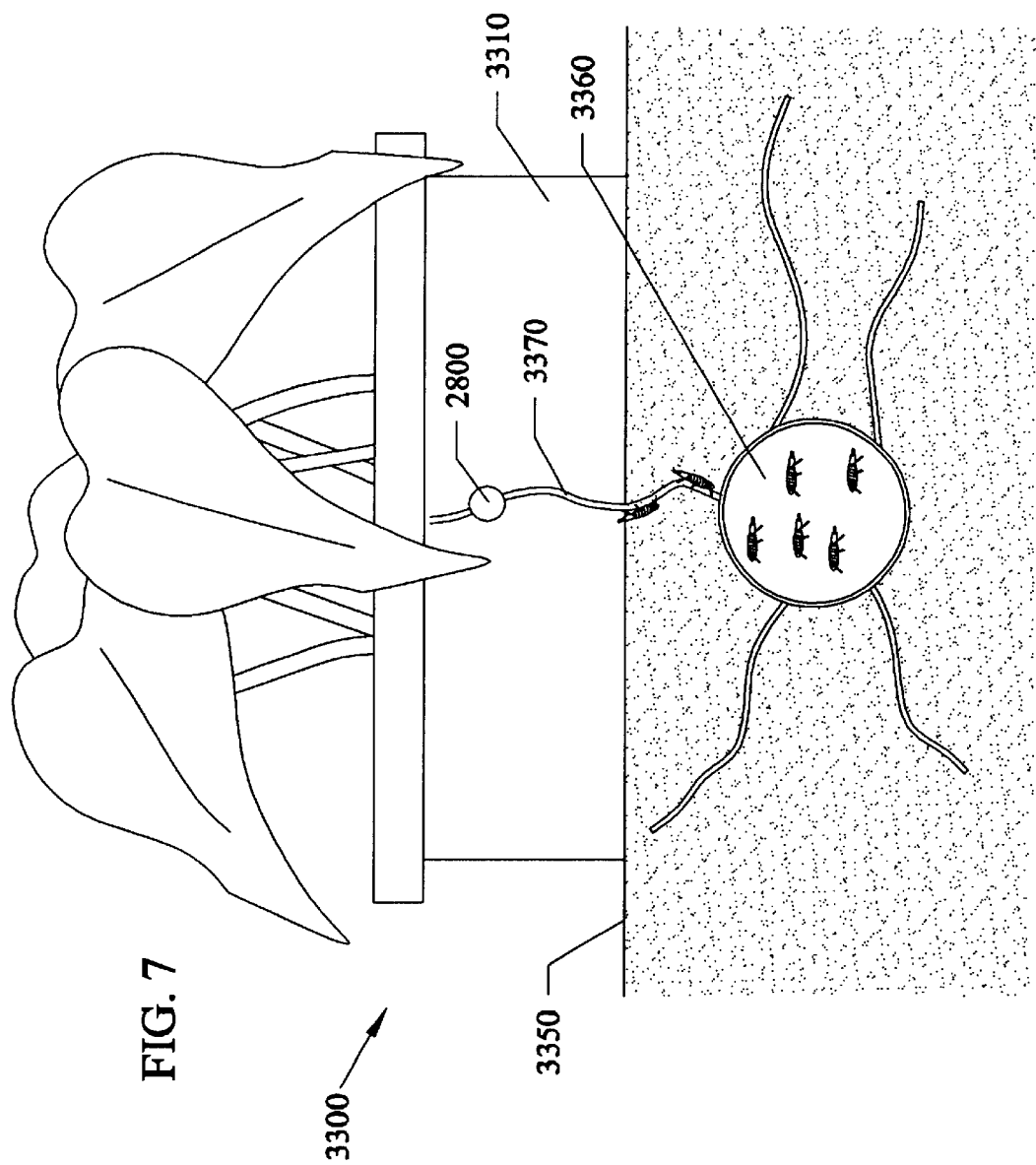
FIG. 7 shows the preferred embodiment of the preceding figures being applied to a planter.

FIG. 7 shows the preferred embodiment of the preceding figures being applied to a planter 3300 holding shrubbery and plants in a garden. Colonies of arthropods 3360 such as termites, below ground surface 3350 are known to build above ground tunnels 3370 on sides of planters 3310, such as wooden planters, and the like, in order to travel to edible food sources in on the planters 3310.

Referring to FIG. 7, placing the above ground chamber 2800 with its' open end and fastening member surface onto the side of the planter 3300 can be an attractant food source for the termites. Furthermore, placing the novel above ground chamber directly in the path of a known above ground tunnel 3370 can have the effect of interrupting the travel route of the crawling arthropods from damaging the planter 300 and any arthropod edible items inside of the planter 3300. As previously described, arthropods, such as subterranean termites will bring the slow-acting non-repellent toxicants back to their spaces 2960 such as their galleries and colonies which will kill the arthropods over time.

Second Embodiment

Figure 8:
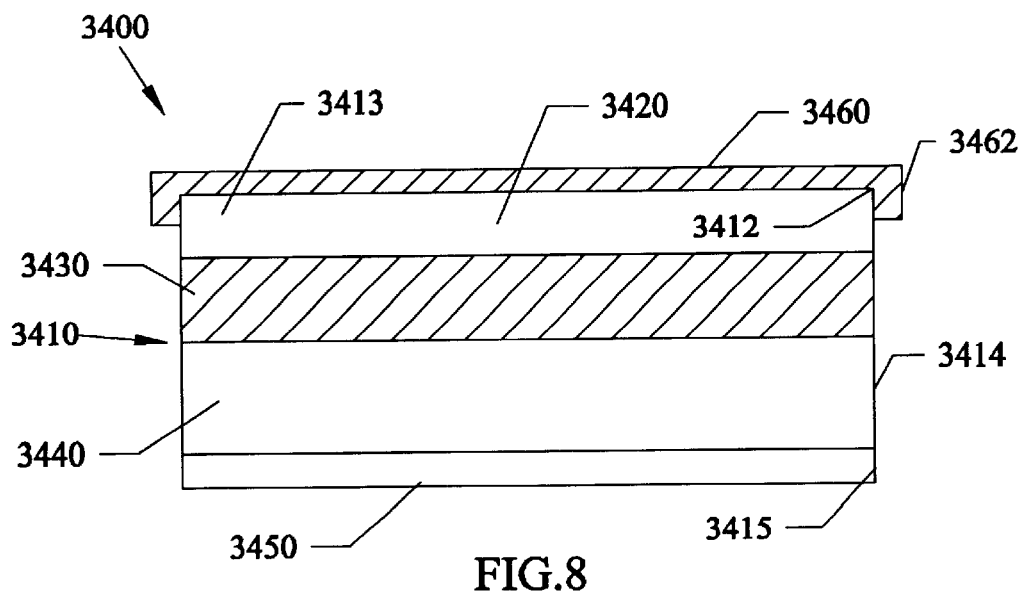
FIG. 8 shows a second preferred embodiment of the above ground invention for arthropod control having a chamber with a snap top.

FIG. 8 shows a second preferred embodiment 3400 of the above ground invention for arthropod control having a chamber 3410 with a snap top 3460. Referring to FIG. 8, removable cap end 3460 can have perimeter overhanging edges 3462 for snapably fitting over the top edges 3412 of chamber 3410 for allowing the chamber 3400 to be reusable over time. Chamber 3410 can be a cylindrical disc, plastic petri dish, and the like, and can have an open top end 3413, closed sides 3414, open bottom 3415, having dimensions of approximately 5 cm in diameter and approximately 1.3 cm in height.

Covering upper open end 3413 of chamber 3410 can be a removable lid 3460 which can snap onto upper edge 3412 of open end 3413. The removable lid allows for the contents of the chamber 3410 to be replaced over time so that the chamber 3410 can be reused without having to remove the entire assembled chamber 3400 from any surface that it was previously being applied to.

The removable lid type cap 3460, and/or the entire chamber 3410 can be made of a nonopaque material to allow users to see the contents inside the chamber 3410. Inside the chamber 3410 against the removable top 3413, can be a thin layer 3420 of an edible food source such as cellulose, and the like. Underneath the layer 3420 can be a foraging matrix 3430 having a thickness of approximately 7 cm and a diameter slightly less than that of the chamber 3410. The foraging matrix 3430 can consist of non-edible particles mixed with a slow-acting non-repellent toxicant such as that previously described above. Underneath the foraging matrix 3430 can be a disc layer 3440 of an edible non-toxic food source such as foam, and the like. The disc layer 3440 can have a thickness of approximately 1.2 cm and a diameter barely slightly smaller than the diameter of the chamber 3410 so that the disc layer tightly fits within the bottom open end 3415 of the chamber 3410.

Covering the outer exposed side of the disc 3440 can be a fastening member 3450 which allows the chamber to be fastened to various support surfaces. The fastening member can be an adhesive layer. The fastening member can be peel and stick tape, which allows the chamber to easily be applied when needed. The fastening member can be a removable and reusable fastener such as but not limited to hook and loop fasteners, and the like. This embodiment 3400 can be applied to all the indoor, outdoor and manmade and natural structures and items as shown and described in the previous figures.

Third Embodiment

Figure 9:
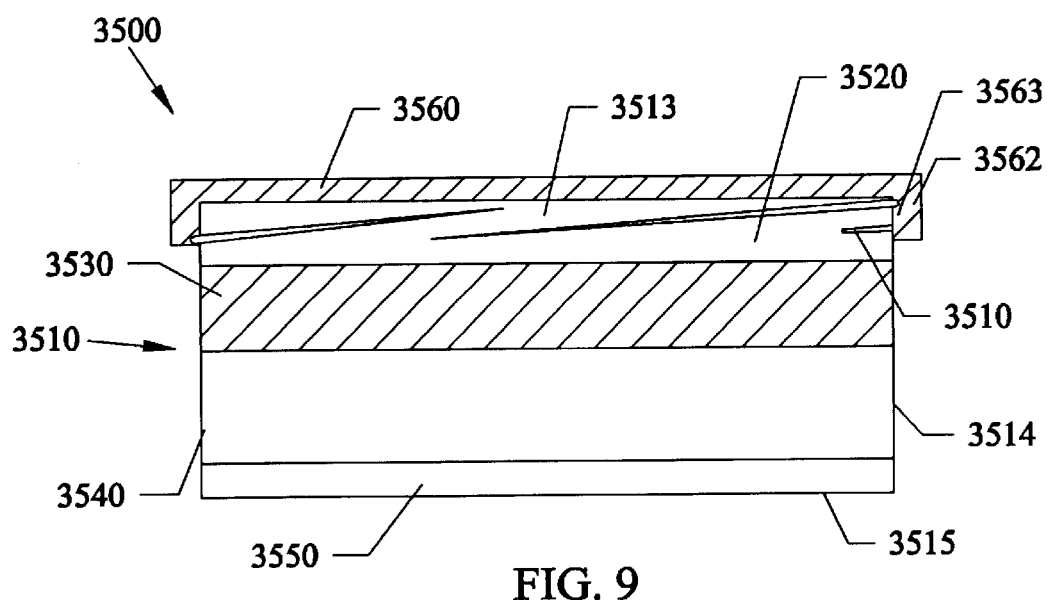
FIG. 9. shows a third preferred embodiment of the above ground invention for arthropod control having a chamber with a screw top.

FIG. 9. shows a third preferred embodiment 3500 of the above ground invention for arthropod control having a chamber 3510 with a screw top 3560. Referring to FIG. 9, removable cap 3560 can have perimeter overhanging edges 3562 with interior facing threads 3563 for allowing the cap 3560 to be able to screw onto and about exterior threaded upper walls 3510 of chamber 3510 for allowing the chamber 3500 to be reusable over time. Chamber 3510 can be a cylindrical disc, plastic petri dish, and the like, and can have an open top end 3513, closed sides 3514, open bottom 3515, having dimensions of approximately 5 cm in diameter and approximately 1.3 cm in height.

The removable lid type cap 3560 allows for the contents of the chamber 3510 to be replaced over time so that the chamber 3510 can be reused without having to remove the entire assembled chamber 3500 from any surface that it was previously applied to.

The removable lid 3560, and/or the entire chamber 3510 can be made of a non-opaque material to allow users to see the contents inside the chamber 3510. Inside the chamber 3510 against the removable top 3513, can be a thin layer 3520 of an edible food source such as cellulose, and the like. Underneath the layer 3520 can be a foraging matrix 3530 having a thickness of approximately 7 cm and a diameter slightly less than that of the chamber 3510. The foraging matrix 3530 can consist of non-edible particles mixed with a slow-acting non-repellent toxicant such as that previously described above. Underneath the foraging matrix 3530 can be a disc layer 3540 of an edible non-toxic food source such as foam, and the like. The disc layer 3540 can have a thickness of approximately 1.2 cm and a diameter barely slightly smaller than the diameter of the chamber 3510 so that the disc layer tightly fits within the bottom open end 3515 of the chamber 3510.

Covering the outer exposed side of the disc 3540 can be a fastening member 3550 which allows the chamber to be fastened to various support surfaces. The fastening member can be an adhesive layer. The fastening member can be peel and stick tape, which allows the chamber to easily be applied when needed. The fastening member can be a removable and reusable fastener such as but not limited to hook and loop fasteners, and the like. This embodiment 3500 can be applied to all the indoor, outdoor and manmade and natural structures and items as shown and described in the previous figures.

Fourth Embodiment

Figure 10:
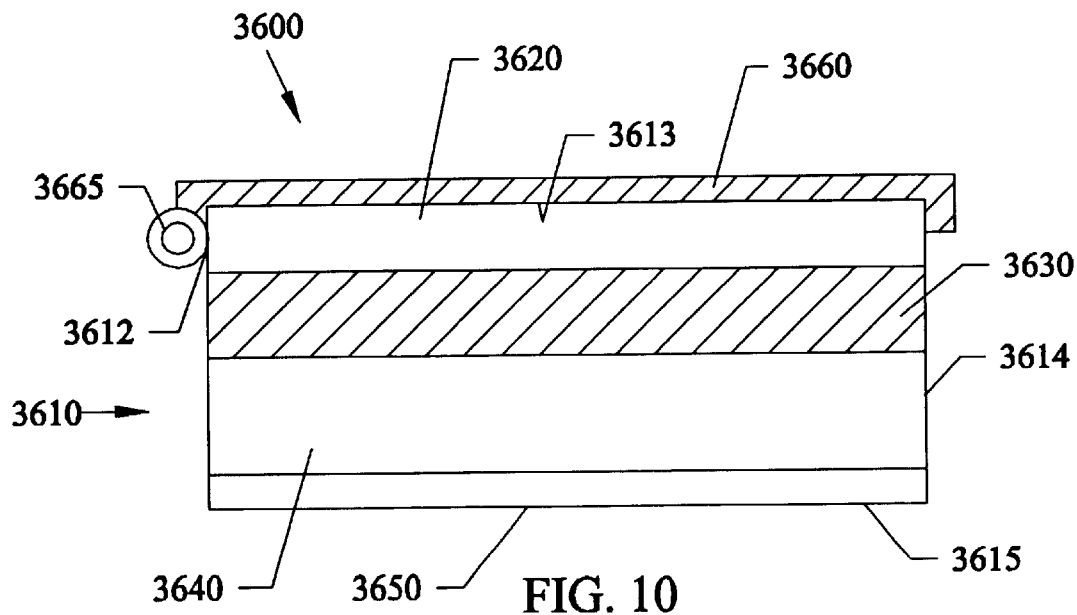
FIG. 10 shows a fourth preferred embodiment of the above ground invention for arthropod control having a chamber with a hinged top.

FIG. 10 shows a fourth preferred embodiment 3600 of the above ground invention for arthropod control having a chamber 3610 with a hinged top 3660. Referring to FIG. 10, removable cap 3660 can have a hinged end 3665 for allowing the cap 3660 to be able to hingedly attach to an upper wall portion 3612 of chamber 3610 for allowing the chamber 3600 to be reusable over time. Chamber 3610 can be a cylindrical disc, plastic petri dish, and the like, and can have an open top end 3613, closed sides 3614, open bottom 3615, having dimensions of approximately 5 cm in diameter and approximately 1.3 cm in height.

The removable lid type cap 3660 allows for the contents of the chamber 3610 to be replaced over time so that the chamber 3610 can be reused without having to remove the entire assembled chamber 3600 from any surface that it was previously being applied to.

The removable lid 3660, and/or the entire chamber 3610 can be made of a non-opaque material to allow users to see the contents inside the chamber 3610. Inside the chamber 3610 against the removable top 3613, can be a thin layer 3620 of an edible food source such as cellulose, and the like. Underneath the layer 3620 can be a foraging matrix 3630 having a thickness of approximately 7 cm and a diameter slightly less than that of the chamber 3610. The foraging matrix 3630 can consist of non-edible particles mixed with a slow-acting non-repellent toxicant such as that previously described above. Underneath the foraging matrix 3630 can be a disc layer 3640 of an edible non-toxic food source such as foam, and the like. The disc layer 3640 can have a thickness of approximately 1.2 cm and a diameter barely slightly smaller than the diameter of the chamber 3510 so that the disc layer tightly fits within the bottom open end 3615 of the chamber 3610.

Covering the outer exposed side of the disc 3640 can be a fastening member 3650 which allows the chamber to be fastened to various support surfaces. The fastening member can be an adhesive layer. The fastening member can be peel and stick tape, which allows the chamber to easily be applied when needed. The fastening member can be a removable and reusable fastener such as but not limited to hook and loop fasteners, and the like. This embodiment 3600 can be applied to all the indoor, outdoor and manmade and natural structures and items as shown and described in the previous figures.

Fifth Embodiment

Figure 11:
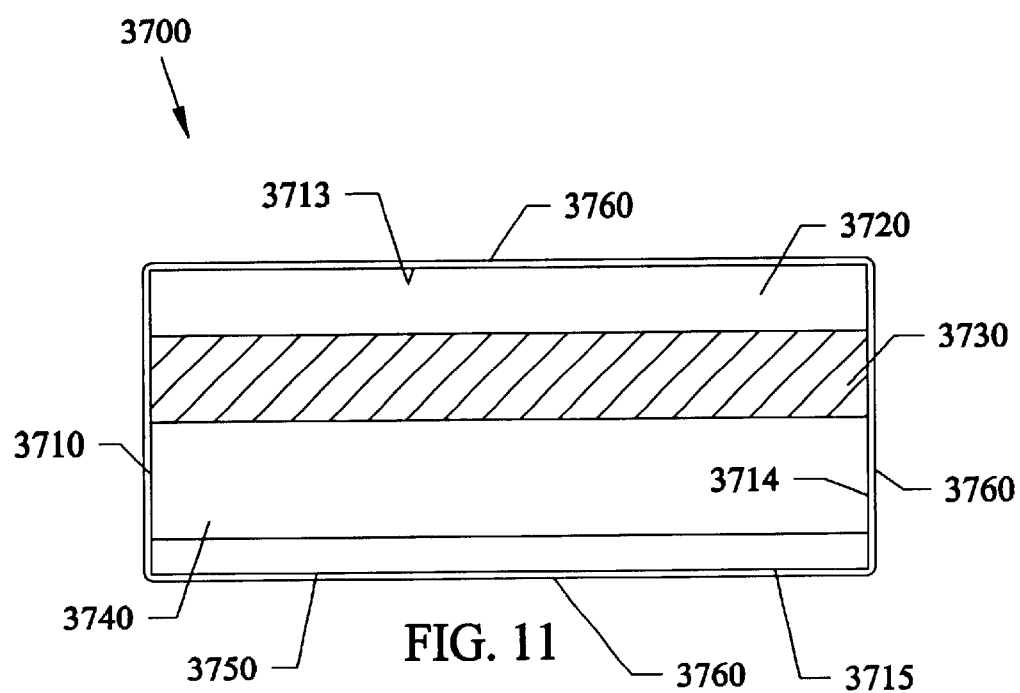
FIG. 11 shows a fifth preferred embodiment of the above ground invention for arthropod control with a shrink-wrapped chamber.

FIG. 11 shows a fifth preferred embodiment 3700 of the above ground invention for arthropod control with a shrink wrapping 3760 about the chamber 3710. Referring to FIG.

11, a shrink wrap type layer 3760 can be wrapped about all sides and the top and bottom of chamber 3710. The shrink wrap 3760 can allow the embodiment 3700 to be easily sold and handled without users having to come into direct contact with the chamber and its' contents. When being used, the shrink wrap 3760 can be fully or partially removed from about the chamber 3710. For example, a portion of the shrink wrap 376 can be removed from the upper open end 3713 of chamber 3710 for allowing the chamber 3710 to be reusable over time. Chamber 3710 can be a cylindrical disc, plastic petri dish, and the like, and can have an open top end 3713, closed sides 3714, open bottom 3715, having dimensions of approximately 5 cm in diameter and approximately 1.3 cm in height.

Removing some or all of the shrink wrap 3760 allows the chamber 3710 can be reused without having to remove the entire assembled chamber 3700 from any surface that it was previously being applied to.

The chamber 3710 can be made of a nonopaque material to allow users to see the contents inside the chamber 3710. Inside the chamber 3510 can be a thin layer 3720 of an edible food source such as cellulose, and the like. Underneath the layer 3720 can be a foraging matrix 3730 having a thickness of approximately 7 cm and a diameter slightly less than that of the chamber 3710. The foraging matrix 3730 can consist of non-edible particles mixed with a slow-acting non-repellent toxicant such as that previously described above. Underneath the foraging matrix 3730 can be a disc layer 3740 of an edible non-toxic food source such as foam, and the like. The disc layer 3740 can have a thickness of approximately 1.2 cm and a diameter barely slightly smaller than the diameter of the chamber 3710 so that the disc layer tightly fits within the bottom open end 3715 of the chamber 3710.

Covering the outer exposed side of the disc 3740 can be a fastening member 3750 which allows the chamber to be fastened to various support surfaces. Accessing the fastening member 3750 can be accomplished after removing at least a portion of the shrink wrap 3760 covering the bottom open end 3715 of the chamber, 3710. The fastening member can be an adhesive layer. The fastening member 3750 can be peel and stick tape, which allows the chamber to easily be applied when needed. Additionally, the fastening member can be a removable and reusable fastener such as but not limited to hook and loop fasteners, and the like. This embodiment 3700 can be applied to all the indoor, outdoor and manmade and natural structures and items as shown and described in the previous figures.

Sixth Embodiment

Figure 12:
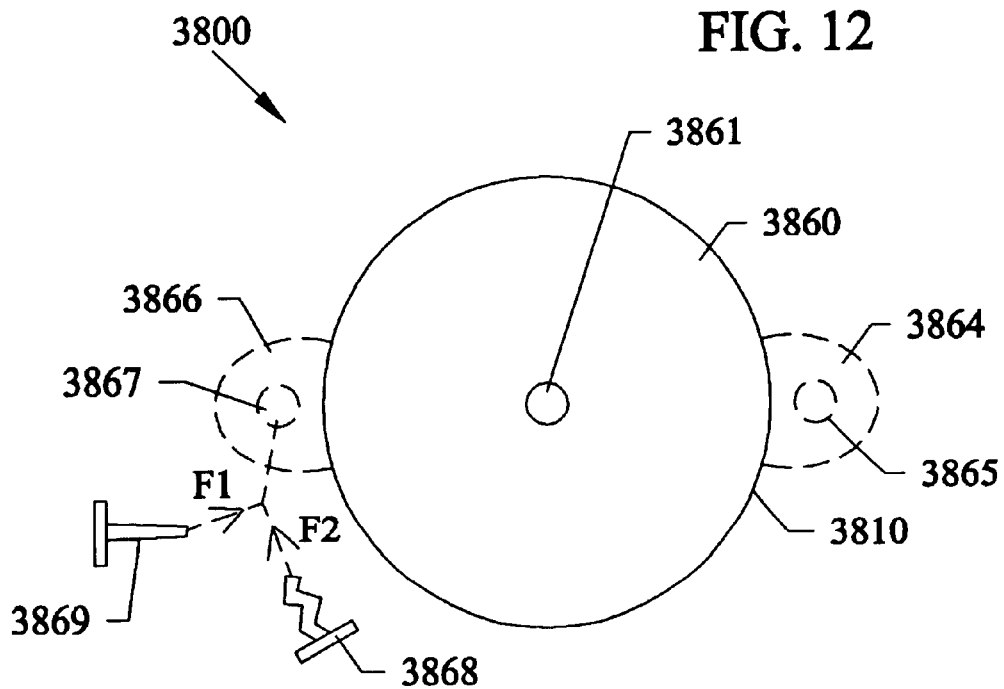

FIG. 12 shows a sixth embodiment 3800 of the above ground invention for allowing the invention to be physically attached to natural structures such as trees, and the like. Embodiment 3800 can include a chamber, with internal layers such as those described in the previous embodiments and can use a modified lid cap cover 3860 which can be snapped on, screwed on, hingedly attached and the like. Here lid cap type cover 3860 can include a center through-hole 3861 that allows fasteners 3868, 3869 such as but not limited to nails and screws to pass therethrough for allowing the embodiment 3800 to be physically fastened and secured onto a support surface where arthropod control is being applied. Additionally, off the sides of chamber portion 3810 of the embodiment 3800 can be exterior protruding tabs 3864, 3866 with through-holes 3865, 3867 for also allowing fasteners 3868, 3869 to pass therethrough for securing the embodiment to a support surface. Embodiment 12 can be used for attaching to any support surface such as manmade and natural structures and items such as but not limited to any of those previously described above.

Seventh Embodiment

Figure 13:
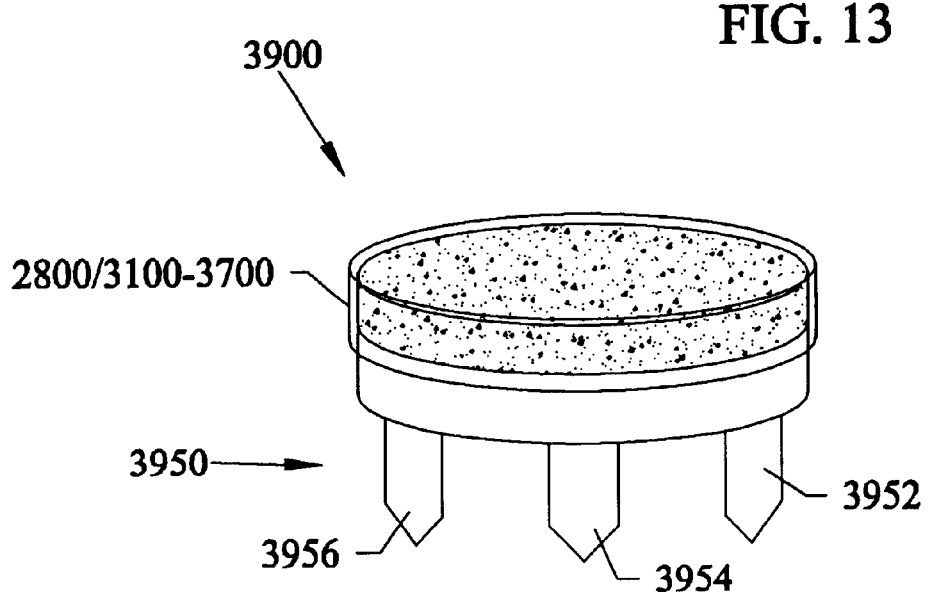
FIG. 13 shows a sixth embodiment of the above ground invention with downwardly protruding stake member(s).

FIG. 13 shows a seventh embodiment 3900 of the above ground invention having pre-attached stake(s) 3950 for allowing the invention to be securely fastened for arthropod control. Embodiment 3900 can include any of the chamber assemblies 2800 and 3100–3700 of those previous described. Here, a pre-attached or premolded downwardly protruding stake type portion 3950 can be used for fastening the embodiment. For example, the stake member(s) 3950 can be premolded from the sides of the chamber, and or premolded into the cap type lid portions of the embodiment 3900. Additionally, the stake member(s) can be pre-inserted into the foam type layers in the embodiment 3900. The fastening member portion 3950 can be a single stake type member, plural stake members 3952, 3954, and 3956. Additionally, the shape of the fastening member portion 3950 can be shaped as one or more teeth members, and the like that can protrude slightly and up to several centimeters beneath the embodiment 3900. In use the sharpened tip(s) of the fastening member 3950 can be pressed or pushed onto the support surface where arthropod treatment control is used for any of the applications previously described above.

FIG. 14 shows an example of using the embodiments 3800 of FIG. 12 and 3900 of FIG. 13 and/or anyone of the preceding embodiments 2800, 3100–3700 for mounting to various locations on a tree 3890.

Although the preceding embodiments refer to the term foam, this layer can also include but not be limited to various types of foams such as but not limited to open cell foam, closed cell foam, Styrofoam, and the like, and combinations, thereof.

Although some types of non-edible foraging matrix materials were described, other types of non-edible foraging matrix materials can be used, such as but not limited to soil, sand, gravel, rocks, pebbles, shale, expanded shale, clay, and the like, and combinations thereof. Additionally, other non-edible foraging matrix materials can be used such as those that can be ground or fashioned to the particle size that arthropods such as but not limited to termites and other arthropods can pick up and can forage through. Additionally, any other types of non-edible foraging materials that arthropods such as but not limited to termites, can be used such as but not limited to dental cast-stone and other porous materials, and the like, and combinations thereof with any other materials described here.

While various shapes for the embodiments are shown, the invention can include all types of geometrical shapes such as but not limited to rectangular, polygon, disc, global, cylindrical, triangular, and the like, and various combinations thereof, and the like.

Although each of the embodiments is separately described above, each and every feature of the embodiments can be interchanged and used with any of the other embodiments. Likewise, each of the embodiments can be used in different combinations with each other.

In addition to the slow-acting non-repellent toxicants previously described, other slow-acting toxicants can also be used such as those listed but not limited to those in Table 2.

TABLE 2

Additional Slow-Acting Toxicants

| TYPE | SLOW-ACTING TOXICANTS |
|---|---|
| Non-repellants: | Chlorfenapyr, Imidacloprid, Friponil |
| Bait Materials: | Hydramethylnon, Sulfluramid, Hexaflumuron |
| IGRs: | Pyriproxyfen, methoprene and lufenuron, dimilin |
| Others: | Chlorpyrifos, and their active derivatives |
| Botanicals: | Neem(azadiractin) |
| Inorganics: | Boric acid based. |

Although the layer in the chamber adjacent to the arthropod entry is described as primarily being an edible non-toxic food source, the layer can also be an arthropod attractant material that arthropods do not necessarily eat, but are attracted to such as pseudo-scents, and the like.

While the preferred embodiments have been described as being used adjacent to structures such as manmade structures such as wood-containing houses, wood-containing buildings, wood-containing sheds and wood-containing fences, and the like, and combinations thereof, the invention embodiments can be placed adjacent to other non manmade items that can be damaged by arthropods, such as but not limited to trees, plants, shrubbery, gardens, and the like, and combinations thereof. Likewise the invention embodiments can be placed adjacent to both manmade and natural items that can be damaged by the arthropods.

Although some of the preferred embodiments have been described as being specifically used with subterranean type termites, the invention embodiments are applicable to other types of crawling arthropods, such as but not limited to termites, carpenter ants, fire ants, roaches, and the like, and combinations, thereof, and the like.

Although the invention embodiments are described as being used primarily with crawling type arthropods, the invention can be used with other types of arthropods such as above ground termites, and the like., and in combinations thereof with other non-crawling arthropods. Additionally, the invention embodiments can be used in combination treatments for both crawling and non-crawling arthropods, and the like.

Additionally, the embodiments can be attached directly to materials themselves, such as but not limited to being attached to landscape timbers including recycled railroad ties, which has been known to transport pest species such as Formosan subterranean termites around the country. For example, the teeth and/or stakes and/or nail/screw fasteners of the embodiments can be used for such an attachment.

The invention embodiments can be placed adjacent to either or both manmade and natural items and structures that can be damaged by the arthropods.

While the invention has been described, disclosed, illustrated and shown in various terms of certain embodiments or modifications which it has presumed in practice, the scope of the invention is not intended to be, nor should it be deemed to be, limited thereby and such other modifications or embodiments as may be suggested by the teachings herein are particularly reserved especially as they fall within the breadth and scope of the claims here appended.

We claim:

1. An above ground treatment method of killing arthropods, comprising the steps of:
    (a) providing a chamber with at least one open end, the chamber having at least one layer of a nontoxic food source with one side adjacent to the one open end being accessible to arthropods;
    (b) inserting a foraging non-edible matrix treated with a slow-acting and nonrepellent toxicant into the chamber adjacent to a second side of the one layer of the nontoxic food source opposite to the nontoxic food source;
    (c) mixing the slow-acting and non-repellent toxicant with the foraging non-edible matrix selected from at least one of: soil, gravel, rocks, pebbles, shale, and mixtures thereof; and
    (d) positioning the at least one open end of the chamber adjacent to a surface above ground level, wherein arthropods enter into the at least one open end of the chamber to eat through the non-toxic food source into the toxicant treated non-edible matrix, so that slow-acting and non-repellent toxicant destroys arthropods in their colonies over time.

2. The above ground treatment method of claim 1, wherein the arthropods include at least one of: termites, carpenter ants, fire ants, and roaches.

3. The above ground treatment method of claim 1, further comprising the step of: placing the chamber on the surface of a manmade structure.

4. The above ground treatment method of claim 3, wherein the manmade structure is selected from at least one of: a building, a house, a fence, and a shed.

5. The above ground treatment method of claim 1, further comprising the step of: placing the chamber on the surface of a tree.

6. The above ground treatment method of claim 1, further comprising the step of: placing the chamber on the surface of a planter, the planter holding at least one of: a plant, a garden and a shrub.

7. The above ground treatment method of claim 1, further comprising the step of:
    providing the chamber with a window portion for allowing a portion of interior contents of the chamber to be seen from outside the chamber.

8. The above ground treatment method of claim 1, further comprising the step of:
    replacing a portion of the interior contents of the chamber so that the chamber is reusable over time.

9. The above ground treatment of claim 1, wherein the food source includes the step of:
    placing a nontoxic food source selected from at least one of: wood, paper, cellulose material, foam, plastic, and mixtures thereof, into the open end of the chamber.

10. The above ground treatment method of claim 1, wherein the chamber includes the step of:
    selecting a shape from at least one of: a disc, a cylinder, a rectangle, a triangle, a polygon, and combinations thereof.

11. The above ground treatment method of claim 1, further comprising the step of:
    placing a fastening member adjacent to the nontoxic food source layer in order to allow the chamber to selectively be fastened to various surfaces.

12. The above ground treatment method of claim 1, further comprising the step of:
    placing a peel and stick tape adjacent to the nontoxic food source layer in order to allow the chamber to selectively fastened to various surfaces.

13. The above ground treatment method of claim 1, further comprising the step of:
    placing a hook and loop fasteners adjacent to the nontoxic food source layer in order to allow the chamber to selectively fastened to various surfaces.

14. An above ground apparatus for killing arthropods, comprising in combination:
  a chamber having at least one opening with a layer formed from a non-toxic, edible arthropod food source;
  a foraging non-edible foraging matrix having a slow-acting and non-repellent toxicant within the chamber on an opposite side of the non-toxic edible layer; and
  an exposed portion of a foundation adjacent to the at least one opening for allowing arthropods to enter into and pass out of the chamber to disperse the slow acting and non-repellent toxicant to their colony to kill arthropods over time.

15. The above ground apparatus of claim 14, further comprising:
  a window portion on the chamber for allowing a portion of interior contents of the chamber to be seen from outside the chamber.

16. The above ground apparatus of claim 14, further comprising:
  means for allowing an interior content of the chamber to be replaced so that the chamber is reusable over time.

17. The above ground apparatus of claim 16, wherein the replacement means includes: a cap portion that opens.

18. The above ground apparatus of claim 17, wherein the cap portion includes:
  a cap cover having threads for allowing the cap cover to be screwed on.

19. The above ground apparatus of claim 17, wherein the cap portion includes:
  portions for allowing the cap portion to be snapably attachable and detachable.

20. The above ground apparatus of claim 17, wherein the cap portion includes:
  a hinge member for allowing the cap cover to open and close.

21. The above ground apparatus of claim 14, wherein the nontoxic food source is selected from at least one of: wood, paper, cellulose material, foam, plastic, and mixtures thereof.

22. The above ground apparatus of claim 14, wherein the foraging non-edible matrix is selected from at least one of: soil, gravel, rocks, pebbles, shale, and mixtures thereof.

23. The above ground apparatus of claim 14, wherein the chamber includes a shape selected from at least one of: a disc, a cylinder, a rectangle, a triangle, a polygon, and combinations thereof.

24. The above ground apparatus of claim 14, further comprising:
  a fastening member adjacent to the nontoxic food source layer in order to allow the chamber to selectively be fastened to various surfaces.

25. The above ground apparatus of claim 24, wherein the fastening member includes: an adhesive surface.

26. The above ground apparatus of claim 24, wherein the fastening member includes: peel and stick tape adjacent to the nontoxic food source layer in order to allow the chamber to selectively be fastened to various surfaces.

27. The above ground apparatus of claim 24, wherein the fastening member includes: a removable fastener.

28. The above ground apparatus of claim 27, wherein the removable fastener includes: hook and loop fasteners.

29. The above ground apparatus of claim 24, wherein the fastening member includes: a fastener selected from at least one of a nail and a screw.

30. The above ground apparatus of claim 24, wherein the fastening member includes: a stake.

31. The above ground apparatus of claim 24, wherein the apparatus further includes: at least one pre-existing through-hole for allowing a fastener to be inserted therethrough.

32. The above ground apparatus of claim 14, further comprising:
  a shrink wrap enclosing means about the apparatus, for allowing the apparatus to be safely handled.

33. An above ground apparatus for killing arthropods, comprising in combination:
  a chamber having at least one opening with a layer formed from a non-toxic, edible arthropod food source;
  a foraging non-edible foraging matrix having a slow-acting and non-repellent toxicant within the chamber on an opposite side of the non-toxic edible layer; and
  a side of a fence adjacent to the at least one opening for allowing anthropods to enter into and pass out of chamber to disperse the slow acting and non-repellent toxicant to their colony to kill arthropods over time.

34. An above ground apparatus for killing arthropods, comprising in combination:
  a chamber having at least one opening with a layer formed from a non-toxic, edible arthropod food source;
  a foraging non-edible foraging matrix having a slow-acting and non-repellant toxicant within the chamber on a opposite side of the non-toxic edible layer, the forming non-edible matrix is selected from at least one of; soil sand gravel, rocks, pebbles, shale and mixtures thereof; and
  an above ground surface adjacent to the at least one opening for allowing arthropods to enter into and pass out of the chamber to disperse the slow acting and non-repellent toxicant to their colony to kill arthropods over time.

* * * * *